United States Patent [19]

Hall et al.

[11] Patent Number: 4,827,587

[45] Date of Patent: May 9, 1989

[54] METHOD OF FABRICATING AN AIR COOLED TURBINE BLADE

[75] Inventors: Kenneth B. Hall, Jupiter; Kenneth K. Landis, Tequesta, both of Fla.

[73] Assignee: United Technologies Corporation, Hartford, Conn.

[21] Appl. No.: 147,464

[22] Filed: Jan. 25, 1988

[51] Int. Cl.⁴ .............................................. B21K 3/04
[52] U.S. Cl. ........................... 29/156.8 B; 29/156.8 H; 29/527.6
[58] Field of Search ................. 29/156.8 B, 156.8 H, 29/23.5, 156.8 R, 527.6, 527.5, DIG. 26, DIG. 29, DIG. 5; 415/DIG. 1; 416/97 R, 232, 231 R, 236 R

[56] References Cited

U.S. PATENT DOCUMENTS

| | | | |
|---|---|---|---|
| 3,044,745 | 7/1962 | Stark | 29/156.8 H |
| 3,329,596 | 7/1967 | Abt et al. | 29/156.8 B |
| 3,934,322 | 1/1976 | Hauser et al. | 29/156.8 B |
| 4,042,162 | 8/1977 | Meginnis et al. | 29/156.8 H |
| 4,672,727 | 6/1987 | Field | 29/156.8 R |

FOREIGN PATENT DOCUMENTS 0079285  5/1983  European Pat. Off. ....... 29/156.8 H

Primary Examiner—P. W. Echols
Assistant Examiner—Irene Cuda
Attorney, Agent, or Firm—Edward L. Kochey, Jr.

[57] ABSTRACT

A turbine blade is formed from an airfoil blade 10 having V-grooves 12 in the outer surface and indentations 26 in the inner surface. A slot 30 is machined at the root of the groove intersecting the slots, and providing a smooth flow path for the cooling air discharging along the blade surface.

12 Claims, 2 Drawing Sheets

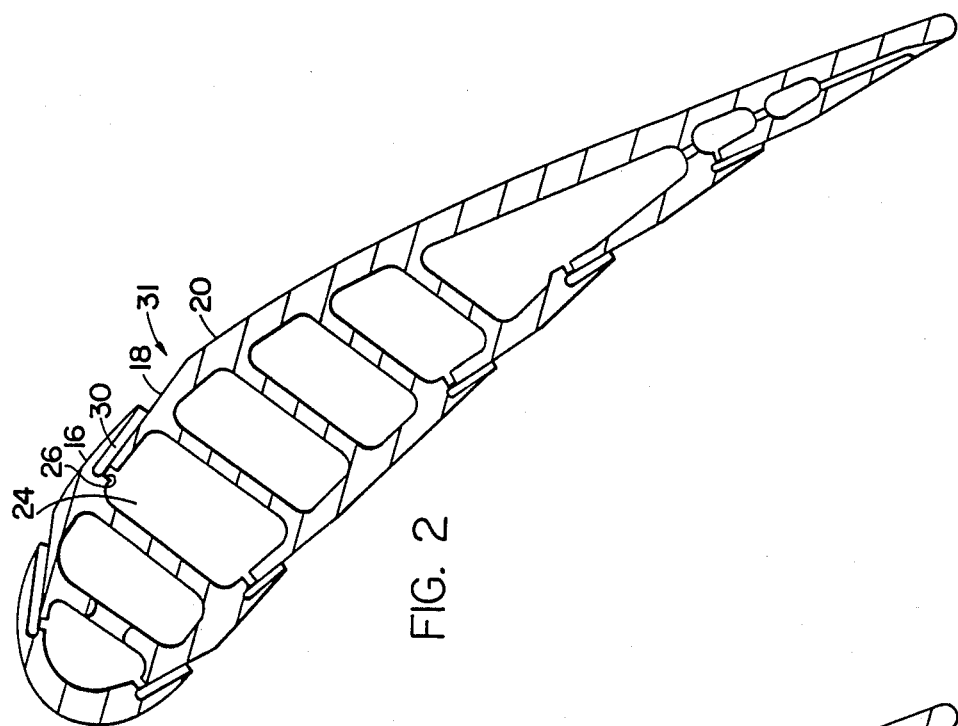
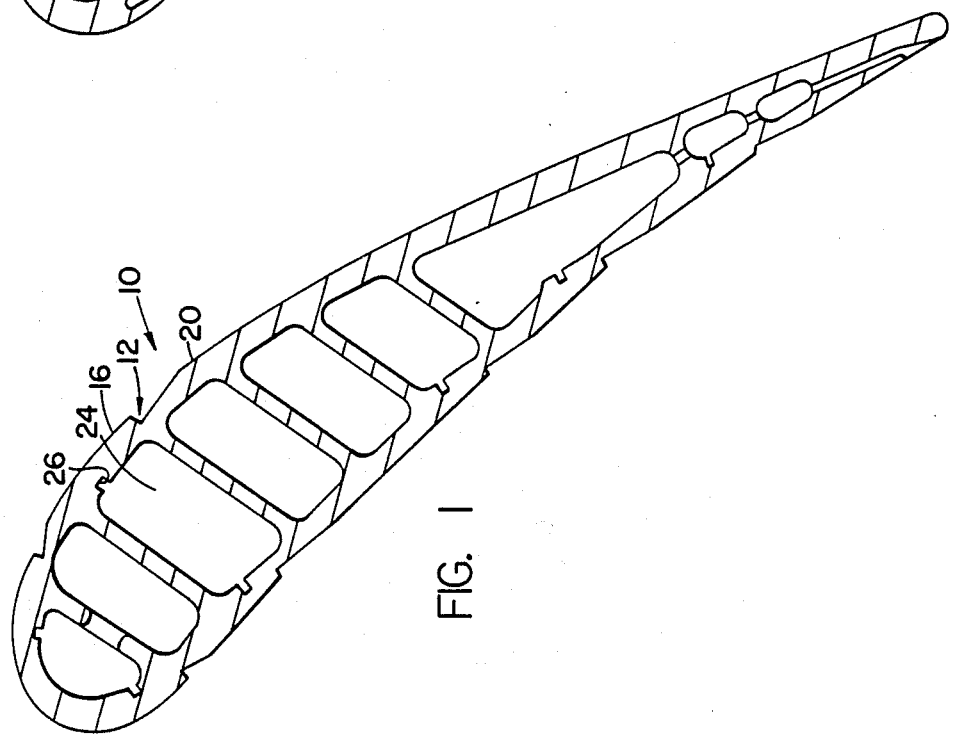

METHOD OF FABRICATING AN AIR COOLED TURBINE BLADE

DESCRIPTION

1. Technical Field

The invention relates to a method of manufacturing air cooled turbine blades and in particular to a method of forming cooling air slots.

2. Background of the Invention

In gas turbines one of the limitations on gas temperature, and therefore efficiency of the gas turbine engine, is the ability of turbine blades to endure the high gas temperatures. It is accordingly known to cool the external surface of airfoils by conducting cooling air through an internal cavity in the blade and through a plurality of small passages discharging the air. It is desirable that the air exiting from these passages remain entrained in the boundary layer on the surface of the airfoil for as long a distance as possible downstream of the passage providing a protecting film of cool air between the hot mainstream gas and the airfoil surface. This use of cooling air itself decreases engine efficiency and therefore it is desirable to use as small an amount as possible of cooling air. Accordingly, the designer is challenged with obtaining maximum cooling with a limited amount of air.

Typically the airflow is metered by small metering openings at the inlet to each air passageway. Since available pressure differential is fixed by other features of the engine design, the flow is established by sizing these holes. Metering at this location also provides appropriate distribution between the various airfoil cooling slots.

The angle which the flow through the passage makes with the airfoil surface and its direction with respect to the hot gas flow are also important factors. It is generally known that the closer that this cooling air comes to being tangent with the surface, the better the cooling effectiveness.

U.S. Pat. No. 4,672,727 uses a plurality of metering holes substantially perpendicular to the airfoil surface, each of which feeds a diverging slot. The diverging slot forms an angle which is recommended as less than 30 degrees with respect to the airfoil surface. Each slot is sufficiently close to the adjacent slot to form a continuous discharge area.

While a small angle with respect to the airfoil surface is desired, practical difficulties in locating and machining the slots limit this angle. It is therefore desirable to have a method whereby the slots may be accurately located and formed in a manner which approaches a straight angle with respect to the airfoil downstream surface.

SUMMARY OF THE INVENTION

An airfoil blank is cast having longitudinally extending skewed V-grooves in the surface. Each groove has a first groove surface which is substantially perpendicular to the outer surface of the airfoil and the second groove surface at an angle less than 20 degrees from the outer surface. A plurality of outwardly extending indentations are cast into the inner surface at a location just upstream of the groove which is on the first groove surface side of the groove. A longitudinal slot is then machined through the first groove surface which is substantially parallel to and coextensive with the second groove surface, this slot being of a depth to intersect the indentations. The use of the groove facilitates machining and provides a precise manner for locating the slot even with an extremely shallow angle.

BRIEF DESCRIPTION OF THE DRAWINGS

FIG. 1 is a sectional view of the cast airfoil blank;

FIG. 2 is a sectional view of the final machined airfoil;

DESCRIPTION OF THE PREFERRED EMBODIMENT

Figure 3:
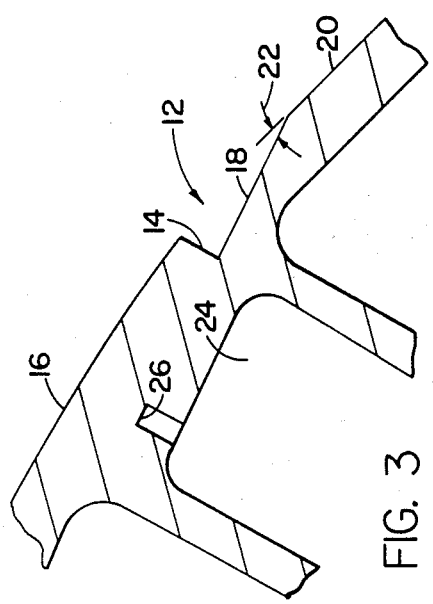
FIG. 3 is a detail of the area of a groove and indentation prior to machining.

An airfoil blank 10 is cast with a plurality of longitudinally extending grooves 12 having a first groove surface 14 which is substantially perpendicular to airfoil surface 16. A second groove surface 18 intersects downstream surface 20 at a small angle 22 which is as small as possible and preferably less than 20 degrees.

The airfoil blank includes a plurality of internal plenums 24 for the passage of cooling air. A plurality of discrete indentations 26 are cast in the inner surface of the airfoil at a spacing of about 50 mils. These indentations may be circular or oval or any other shape, their purpose being predominantly to provide a metering flow passage to later formed slots.

Thereafter segmented slots 30 are electromachined into the blank forming airfoil 31. These slots are 170 mils in length with a 30 mil land 32 between adjacent slots. Land 32 improves the straightening of air flow and also acts to support the cantilever portion 34 of the airfoil blade.

The inner groove surface 36 is coextensive with second groove surface 18 to form a smooth flow path therein. It is preferable that the machining remove some of surface 18 rather than leave a step change at the interface.

The flow area of slot 30 is preferably four times the flow area of the total of holes 26 supplying the slot, with the holes 26 being 14 mils in diameter, while the slot is 8 mils wide by 170 mils long. A larger relative slot area than this results in decreased discharge velocity and a lack of appropriate distribution of the air flow through slots 26 along the length of slot 30. To lower ratio of flow area in the slot destroys the metering effect of this in hole 26.

The trailing edge 38 of cantilevered portion 34 should be as thin as possible since it is known that increased thickness induces turbulence which reduces the effectiveness of the downstream film cooling. Accordingly, with a first groove surface 14 of 10 mils a slot of 8 mils is selected leaving only 2 mils at the trailing edge 38. This preferably should be designed to be less than 3 mils.

Figure 5:
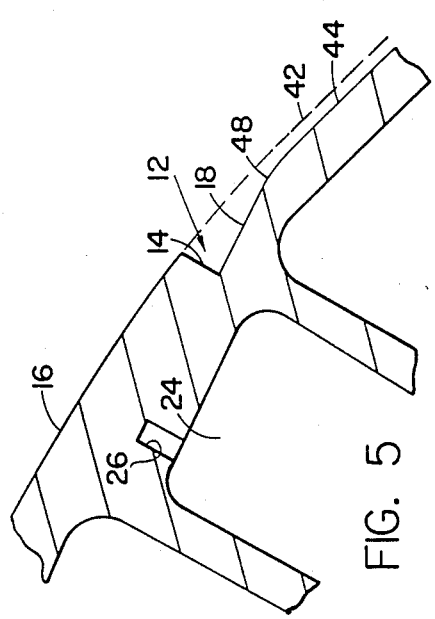
FIG. 5 is a view of the area adjacent to the groove before machining including offset airfoil surfaces.
Figure 6:
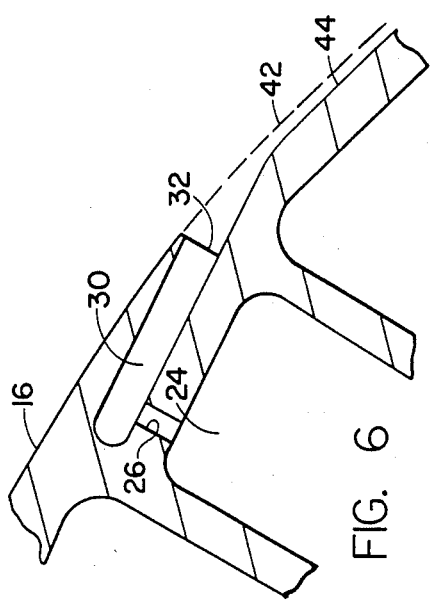
FIG. 6 is a view similar to FIG. 5 after machining.

FIG. 5 illustrates an embodiment where the airfoil surface 16 has a continuous extension 42 which is offset 3 mils from the downstream airfoil surface 44. This offset is related to the thickness of the entry cooling flow, and is preferably between 2 and 10 mils.

A rounded edge 48 of 30 mils phases together the second groove surface 18 with the downstream surface 44. This rounded surface is preferably greater than 25 mils and may be easily cast the same time that groove 12 is. It provides an improved flowpath for the air film to stay against the downstream wall for cooling effectiveness. Furthermore, the offset between surface 16 and 44 provides a natural gap which is filled by this cooling air flow, and this step change is easily cast together with the groove.

Figure 4:
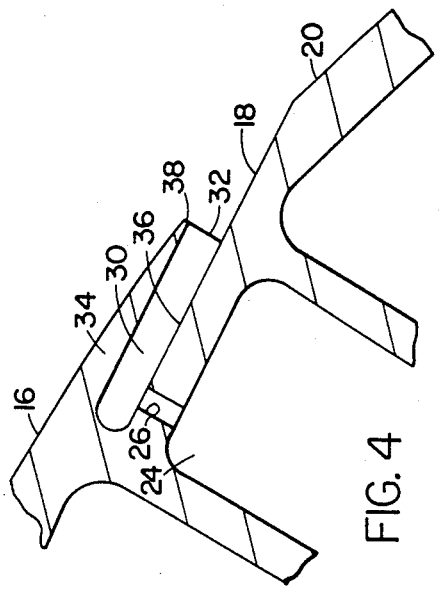
FIG. 4 is a view similar to FIG. 3 after machining.

In a manner similar to FIG. 4, the groove 30 is machined between lands 32 to form the final airfoil structure.

We claim:

1. A method of manufacturing a hollow air cooled longitudinally extending airfoil turbine blade, comprising:

casting an airfoil blank having an outer surface and an inner surface defining a cooling air flow plenum;

forming on said outer surface longitudinally extending skewed V-grooves having a first groove surface substantially perpendicular to said outer surface and a second groove surface at an angle less than 20 degrees from said outer surface in the direction away from said first groove surface;

forming a plurality of outwardly extending indentations in said inner surface at a location adjacent to said V-grooves on the first groove surface side of said V-groove; and forming a longitudinally extending slot through said first groove surface substantially parallel to and coextensive with said second groove surface of a depth to intersect said indentations.

2. The method of claim 1 including;

rounding the edge of the intersection of said second groove surface with said outer surface.

3. The method of claim 2 including:

rounding the edge of the intersection between said second groove surface and said outer surface to a radius greater than 25 mils.

4. The method of claim 1 wherein:

the step of forming on said outer surface longitudinally extending skewed V-grooves comprises casting said grooves in said blank.

5. The method of claim 1 wherein the step of forming a plurality of outwardly extending indentations comprising casting said indentations in said blank.

6. The method of claim 1 wherein the step of forming a longitudinally extending slot comprises:

machining a slot in a plurality of longitudinally extending segments leaving a land of blade material between adjacent segments.

7. The method of claim 1 wherein the step of forming a longitudinally extending slot comprises:

machining said slot of a width with respect to the depth of said first groove surface within 3 mils of said outer surface whereby the edge of the remaining material does not exceed 3 mils in thickness.

8. The method of claim 1 including:

casting said airfoil blank with a step change from a hypothetical continuous extension of said airfoil surface at the location of said grooves.

9. The method of claim 8 including:

forming said blank with a step change between 2 and 10 mils.

10. The method of claim 1 wherein the step of forming a longitudinally extending slot comprises:

machining said slot.

11. A method of manufacturing a hollow air cooled longitudinally extending airfoil turbine blade, comprising:

casting an airfoil blank having an outer surface and an inner surface defining a cooling air flow plenum;

casting in said outer surface longitudinally extending skewed V-grooves having a first groove surface substantially perpendicular to said outer surface and a second groove surface at an angle less than 20 degrees from said outer surface in the direction away from said first groove surface;

casting a plurality of outwardly extending indentations in said inner surface at a location adjacent to said V-grooves on the first groove surface side of said V-groove; and forming a longitudinally extending slot in a plurality of longitudinally extending segments leaving a land of blade material between adjacent segments, said slots being of a width less than the width of said first groove surface and substantially parallel to and coextensive with said second groove surface of a depth to intersect said indentations.

12. A method of manufacturing a hollow air cooled longitudinally extending airfoil turbine blade, comprising:

casting an airfoil blank having an outer surface and an inner surface defining a cooling air flow plenum;

casting in said outer surface longitudinally extending skewed V-grooves having a first groove surface substantially perpendicular to said outer surface and a second groove surface at an angle less than 20 degrees from said outer surface in the direction away from said first groove surface, with a step change from a hypothetical continuous extension of said airfoil surface at the location of said grooves;

forming a plurality of outwardly extending indentations in said inner surface at a location adjacent to said V-grooves on the first groove surface side of said V-groove; and forming a longitudinally extending slot in a plurality of segments leaving a land of blade material between adjacent segments, said slots being of a width less than the width of said first groove surface and substantially parallel to and coextensive with said second groove surface of a depth to intersect said indentations.

* * * * *